US010881837B2

(12) United States Patent
Schibli et al.

(10) Patent No.: US 10,881,837 B2
(45) Date of Patent: Jan. 5, 2021

(54) GUIDEWIRE SYSTEM

(71) Applicant: Heraeus Deutschland GmbH & Co. KG, Hanau (DE)

(72) Inventors: Stefan Schibli, Frankfurt am Main (DE); Jens Troetzschel, Ronneburg (DE); Ronald Von Wald, Centerville, MN (US)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 852 days.

(21) Appl. No.: 15/619,244

(22) Filed: Jun. 9, 2017

(65) Prior Publication Data

US 2017/0354801 A1 Dec. 14, 2017

(30) Foreign Application Priority Data

Jun. 9, 2016 (EP) .................................... 16173647

(51) Int. Cl.
*A61M 25/09* (2006.01)
*A61B 5/0215* (2006.01)
*A61B 34/20* (2016.01)
*A61B 34/00* (2016.01)
*A61B 5/00* (2006.01)
(Continued)

(52) U.S. Cl.
CPC ..... *A61M 25/09041* (2013.01); *A61B 5/0215* (2013.01); *A61B 5/6851* (2013.01); *A61B 8/0841* (2013.01); *A61B 34/20* (2016.02); *A61B 34/76* (2016.02); *A61M 25/0108* (2013.01); *A61B 2034/2063* (2016.02); *A61B 2090/065* (2016.02); *A61B 2090/3788* (2016.02); *A61M 2025/09108* (2013.01); *A61M 2205/0294* (2013.01)

(58) Field of Classification Search
CPC ........ A61M 25/09041; A61M 25/0108; A61M 2025/09108; A61M 2205/0294; A61B 5/0215; A61B 5/6851; A61B 34/20; A61B 34/76; A61B 8/0841; A61B 2034/2063; A61B 2090/065; A61B 2090/3788
See application file for complete search history.

(56) References Cited

U.S. PATENT DOCUMENTS 6,285,866 B1 * 9/2001 Lee .................. H03B 5/326
29/25.35
2005/0277839 A1 12/2005 Alderman et al.
(Continued)

FOREIGN PATENT DOCUMENTS

| EP | 1837638 | 9/2007 |
| WO | 03030752 | 4/2003 |
| WO | 2015097251 | 7/2015 |

*Primary Examiner* — Peter Luong
(74) *Attorney, Agent, or Firm* — Dicke, Billig & Czaja, PLLC

(57) ABSTRACT

One aspect relates to a guidewire system, a measuring system, and a method for manufacturing such guidewire system. The guidewire system includes a guidewire and a surface acoustic wave sensor device. A portion of a surface of the guidewire is coated by the surface acoustic wave sensor device. The surface acoustic wave sensor device may be configured for measuring a pressure change. The surface acoustic wave sensor device includes a piezoelectric substrate and a transducer. A thickness of the surface acoustic wave sensor device perpendicular to a longitudinal direction of the guidewire is smaller than 100 μm.

10 Claims, 3 Drawing Sheets

(51) Int. Cl.
*A61B 8/08* (2006.01)
*A61M 25/01* (2006.01)
*A61B 90/00* (2016.01)

(56) References Cited

U.S. PATENT DOCUMENTS

| | | | |
|---|---|---|---|
| 2007/0220986 A1* | 9/2007 | Smith | B60C 23/0408 73/727 |
| 2009/0192412 A1* | 7/2009 | Sela | A61M 25/0905 600/585 |
| 2010/0305476 A1 | 12/2010 | Thornton et al. | |

* cited by examiner

GUIDEWIRE SYSTEM

CROSS-REFERENCE TO RELATED APPLICATIONS

This Utility Patent Application claims priority to European Patent Application No. EP 16173647.5, filed on Jun. 9, 2016, which is incorporated herein by reference.

BACKGROUND

One aspect relates to a guidewire system, a measuring system, and a method for manufacturing such guidewire system.

WO 03/030752 A1 discloses catheter lesion diagnostics. A diagnostic apparatus includes an expandable catheter comprising a catheter body having an expandable portion. The expandable portion includes a plurality of spaced piezoelectric elements and a controller that controllably produces and receives a signal from elements of said plurality of spaced piezoelectric elements.

Catheters and guidewires represent the hands of a physician inside a patient body and in particular inside the human vasculature. The haptic feel of the guidewire is therefore important to, for example, safely reach a predetermined location in the body for a predetermined treatment of the patient. However, this haptic feel may be deteriorated by the use of sensor elements. As a result, the haptic feel of guidewires with sensor elements needs to be improved.

Hence, there may be a need to provide an improved guidewire system with enhanced handiness.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the embodiments are evident from the claims, the description provided hereinafter, and the drawings. The embodiments are illustrated through several examples in the drawings. In this context, equal or functionally equal or functionally corresponding elements are identified through the same reference numbers. The invention shall not be limited to the exemplary embodiments.

Exemplary embodiments of the invention will be described in the following with reference to the accompanying drawings.

DETAILED DESCRIPTION

Figure 1:
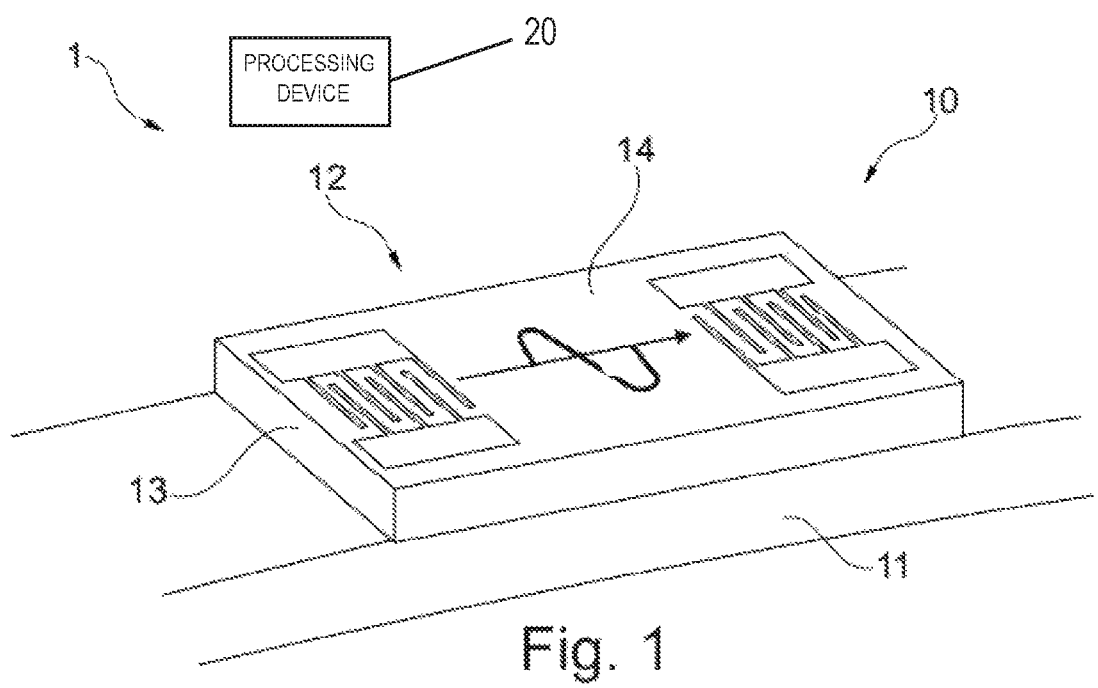
FIG. 1 illustrates a schematic drawing of an example of a measuring system according to one embodiment.

In the following Detailed Description, reference is made to the accompanying drawings, which form a part hereof, and in which is included by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the embodiment. The following detailed description, therefore, is not to be taken in a limiting sense, and the scope of the embodiment is defined by the appended claims.

It is to be understood that the features of the various exemplary embodiments described herein may be combined with each other, unless specifically noted otherwise.

It should be noted that the aspects of the embodiments described in the following apply also to the guidewire system, the measuring system, and the method for manufacturing such guidewire system.

According to one embodiment, a guidewire system is presented. The guidewire system includes a guidewire and a surface acoustic wave sensor device. A portion of a surface of the guidewire is coated by the surface acoustic wave sensor device. The surface acoustic wave sensor device includes a piezoelectric substrate and a transducer. A thickness of the surface acoustic wave sensor device perpendicular to a longitudinal direction of the guidewire is smaller than 100 µm.

The guidewire system according to one embodiment allows integrating a sensor device in a guidewire without changing the haptic feel of the guidewire. This may be achieved by using a surface acoustic wave sensor device as sensor device, by installing the sensor device by coating and/or by applying the sensor device with a very minor thickness.

The thereby constant and unamended haptic feel and the improved handiness can be used, for example, to locate and/or classify a stenosis or another disease state within arteries and/or veins. The haptic feel may also be used to determine a location for an implantable device within the vasculature, such as a stent, a heart valve or the like.

The wording "surface acoustic wave sensor device" will be abbreviated in the following as SAW sensor device or sensor device. In an example, the sensor device is configured for measuring a pressure change. In an example, the sensor device is configured for measuring a pressure change in front and after a vasoconstriction to for example, perfectly position a stent. The sensor device may be a passive sensor with wireless data and energy transfer. The sensor device may be arranged anywhere on the guidewire and, for example, directly at a distal end of the guidewire.

The guidewire system may include several surface acoustic wave sensor devices distributed on or along the guidewire to precisely locate, for example, a seizure of the vein and therefore to perfectly position a stent. Further, several sensor devices allow a 3D visualization of the measured data and, for example, of the 3D pressure information.

The surface acoustic wave sensor device includes a piezoelectric substrate and a transducer. In an example, the piezoelectric substrate is made of zinc oxide, aluminum nitride, silicon dioxide, barium titanate, lead zirconate titanate, sodium potassium niobat, lithium niobat and/or the like. In an example, the transducer is an interdigital transducer (IDT). The IDT may include printed electrical paths (for example, gold thin-film) provided on a piezoelectric substrate (for example, ZnO thin-film) to form the sensor device. An IDT is a device that may include two interlocking comb-shaped arrays of metallic electrodes (in the fashion of a zipper). These metallic electrodes may be deposited on a surface of a piezoelectric substrate, such as quartz, to form a periodic structure. IDTs function may be to convert electric signals to surface acoustic waves by generating periodically distributed mechanical forces via piezoelectric effect (input transducer). The same principle is applied to the conversion of surface acoustic waves back to electric signals (output transducer).

A thickness of the surface acoustic wave sensor device perpendicular to a longitudinal direction of the guidewire is smaller than 100 µm. In an example, the thickness of the sensor device perpendicular to a longitudinal direction of the guidewire is smaller than 50 µm. In an example, the thickness of the sensor device perpendicular to a longitudinal direction of the guidewire is smaller than 25 µm. These minor thicknesses of the sensor device allow an application of the sensor device on the guidewire without changing the cross section of the guidewire as the sensor device does not form a considerable protrusion on the guidewire and it is further not necessary to for example, introduce a recess for the sensor into the guidewire.

In an example, the sensor device is directly coated on the guidewire. In an example, the sensor device is directly coated on an electrical insulated layer of the guidewire. The electrical insulated layer may be a polymer based hydrophobic/hydrophilic coating. In another example, the sensor device is indirectly coated on an additional, flexible substrate of for example, polyimide and then attached and for example, glued on or around the guidewire.

The coating process is described further below and allows an application of the sensor device on the guidewire without changing the cross section of the guidewire. For example, the cross section remains circular or square. This is achieved by coating the guidewire with a very thin sensor device instead of for example, introducing a recess into the guidewire, for example, for a larger sensor. The coating process further allows an application of the sensor device on the guidewire without changing the mechanical properties of the guidewire. This is achieved by coating the guidewire without the application of heat or other influences harming the guidewire materials. As the cross section and the mechanical properties of the guidewire remain unamended, also the properties and, for example, haptic feel of the entire guidewire system is maintained, which eases the application by a user.

In an example, the guidewire system has a diameter in a range of 0.05 to 1 mm, and in one example, 0.1 to 0.5 mm.

According to one embodiment, also a measuring system is presented. The measuring system includes a processing device and the guidewire system as described above. The processing device is arranged distant to the sensor device of the guidewire system. The processing device is configured for a communication with the sensor device. In an example, the processing device is configured for detecting a position of the sensor device. Therefore, the processing device may be configured to emit at least a signal, to receive the reflected signal(s) and to process a time delay between the emitted and the received signal into a distance or a position of the sensor device.

The guidewire system includes a guidewire and a surface acoustic wave sensor device. A portion of a surface of the guidewire is coated by the surface acoustic wave sensor device. The surface acoustic wave sensor device includes a piezoelectric substrate and a transducer. In an example, the sensor device is configured for measuring a pressure change. The guidewire system may include a plurality of surface acoustic wave sensor devices.

A thickness of the surface acoustic wave sensor device perpendicular to a longitudinal direction of the guidewire is smaller than 100 µm. In an example, the thickness of the sensor device perpendicular to a longitudinal direction of the guidewire is smaller than 50 µm.

According to one embodiment, also a method for manufacturing a guidewire system is presented. It includes the following steps, not necessarily in this order:
a) providing a guidewire, and
b) coating a portion of a surface of the guidewire by a surface acoustic wave sensor device.

The sensor device includes a piezoelectric substrate and a transducer. The thickness of the sensor device perpendicular to a longitudinal direction of the guidewire is smaller than 100 µm.

In an example, the coating step maintains the cross section of the guidewire. This is achieved by coating the guidewire with the very thin sensor device instead of for example, introducing a recess into the guidewire, for example, a larger sensor. In an example, the coating step maintains the mechanical properties of the guidewire. This is achieved by coating the guidewire without the application of heat or other influences harming the guidewire materials or inducing micro structural transformations or defects. In an example, the coating step is therefore a sol-gel process. The sol-gel process may be carried out by means of contacting a substrate to a liquid, for example, by means of immersing into the liquid or by means of spraying the liquid onto the substrate to be coated. Multiple layers can be applied in identical or different manner. Even multiple equal layers can be applied in different manners, that is, for example by means of immersing, in one case, and by means of spraying in another case. The layer or coating is formed by means of depositing particles from a colloidal solution or dispersion.

In another example, the coating step is therefore a sputtering process. The sputtering process may be a chemical vapor deposition (CVD) process and, for example, a low pressure chemical vapor deposition (LPCVD). Thereby, a wafer or substrate is exposed to one or more volatile precursors, which react and/or decompose on the substrate surface to produce the desired deposit. The sputtering process may be a physical vapor deposition (PVD) process which is a vacuum deposition method. Thereby, a vapor of material is produced, which is then deposited on an object to be coated.

It shall be understood that the guidewire system, the measuring system, and the method for manufacturing such guidewire system according to the independent claims have similar and/or identical embodiments, for example, as defined in the dependent claims. It shall be understood further that an embodiment can also be any combination of the dependent claims with the respective independent claim.

Guidewires have application in minimally invasive medical procedures where they are used to guide catheters or other medical devices to a target site within the human or animal body. The guidewire is typically advanced to a desired target site, such as a diagnosis or treatment site, for example the site of a lesion or blockage in a vein or artery or other body lumen. Other interventional medical devices, such as guide catheters, therapeutic catheters, or diagnostic catheters, are introduced over or along the guidewire and directed through sometimes tortuous vasculature to the site of the arterial or venous or other blockage, lesion or treatment site.

Guidewires are used in minimally invasive percutaneous transluminal coronary angioplasty (PTCA) and peripheral angioplasty procedures. In PTCA procedures, a guidewire is typically inserted into the femoral artery of a patient near the groin, advanced over the aortic arch, through a coronary ostium and into a coronary artery to a target site. A guidewire insertion procedure is typically performed in a hospital setting using fluoroscopy to visualize and assist the advancement of the guidewire to the desired target site.

Other medical uses of guidewires include, without limitation, use in urinary, gastro-intestinal, pulmonary and biliary applications. Guidewires are also used in other interventional, investigative and surgical applications and procedures.

The principle function of the known guidewire is to facilitate access to a remote location within a body lumen, thereby making the location of the site available to adjuvant diagnostic or treatment devices. This is achieved by providing the guidewire as a flexible wire which is capable of traversing bodily channels, vessels or passageways (generally referred to as lumens) which are often extremely tortuous. The guidewire is sufficiently flexible to be navigable to the desired site without damaging the walls of the vessels it passes through. Also as mentioned above, once the guidewire has been positioned at the desired location, it is used as a guide over or along which other devices can be accurately guided to or placed at the target site. For example, in balloon angioplasty, a catheter having a balloon at its distal tip is introduced, using the guidewire to guide it, to an area of a blood vessel which is blocked or partially blocked by atherosclerotic deposits (plaque). The atherosclerotic deposits on the vessel wall reduce or prevent blood flow. The balloon is inflated at the site of the plaque to compress the plaque against the vessel wall thereby opening the blocked or partially blocked vessel to the flow of blood. In a related procedure, a stent may be advanced over or along the guidewire to the site of blockage and deployed there to provide an artificial scaffolding which maintains the vessel in the open state in which good blood flow occurs.

FIG. 1 illustrates schematically and exemplarily an embodiment of a measuring system 1. The measuring system 1 includes a processing device 20 and a guidewire system 10.

The guidewire system 10 includes a guidewire 11 and a surface acoustic wave sensor device 12. A portion of a surface of the guidewire 11 is coated with at least one surface acoustic wave sensor device 12 to measure a pressure change. A thickness of the surface acoustic wave sensor device 12 perpendicular to a longitudinal direction of the guidewire 11 is smaller than 100 µm.

The processing device 20 is arranged distant to the surface acoustic wave sensor device 12 of the guidewire system 10. The processing device 20 is configured for a communication with the sensor device 12.

The surface acoustic wave sensor device 12 includes a piezoelectric substrate 13 and a transducer 14. The transducer 14 is an interdigital transducer (IDT). The IDT includes two interlocking comb-shaped arrays of metallic electrodes or antennas and may work as follows. A radio signal induces a current in for example, a first, in FIG. 1 left antenna which induces surface acoustic waves on the piezoelectric substrate 13. The same antenna sends back an echo. A second, in FIG. 1 right antenna is placed on the same piezoelectric substrate 13 and also sends an echo with a time delay due to a defined distance to the first antenna. This time delay depends mainly on an acoustic wave speed on the piezoelectric substrate 13 and the distance. The acoustic wave speed of the substrates may depend on the material, mechanical constrains and/or temperature.

Figure 2:
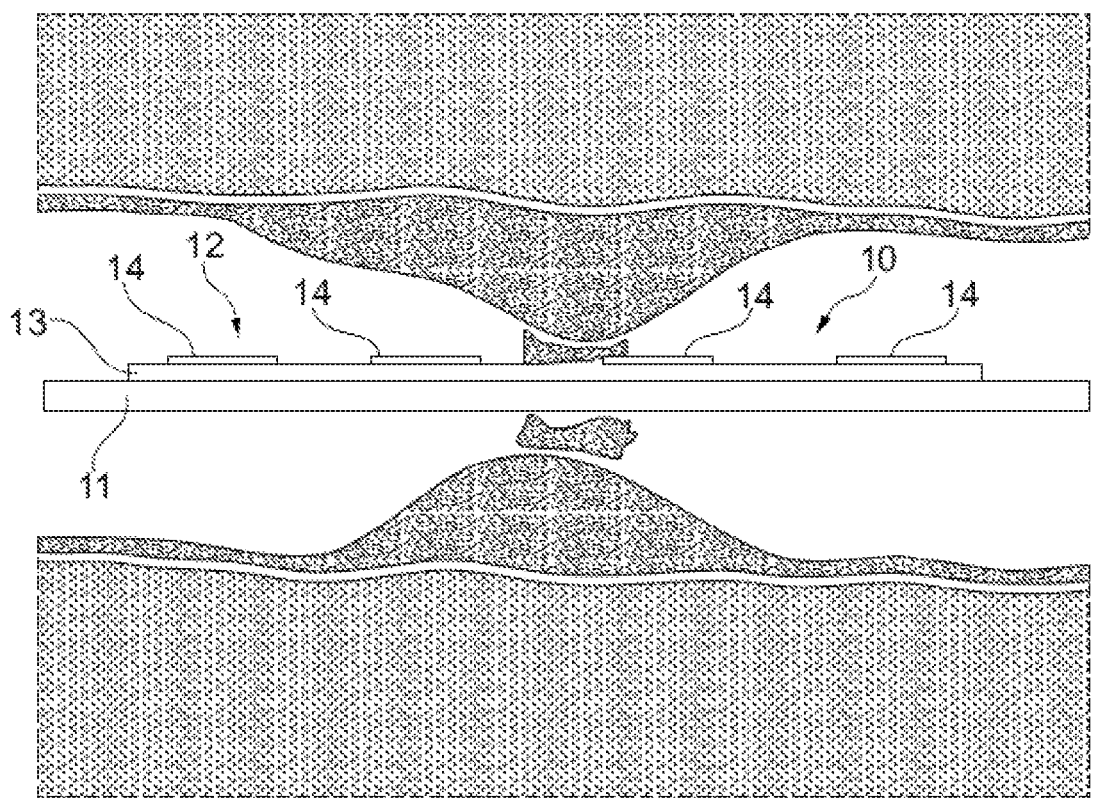
FIG. 2 illustrates schematically and exemplarily an embodiment of a guidewire system 10 according to one embodiment.

FIG. 2 illustrates schematically and exemplarily an embodiment of a guidewire system 10 according to the embodiment. As illustrated in FIG. 2, the guidewire system 10 is configured for measuring a pressure change in front and after a vasoconstriction to for example, perfectly position a stent. A portion of a surface of the guidewire 11 is coated by several surface acoustic wave sensor devices 12. Each or at least some of the surface acoustic wave sensor devices 12 are configured for measuring a pressure change. Each or at least some of the surface acoustic wave sensor devices 12 include a piezoelectric substrate 13 and a transducer 14. The transducer 14 is an interdigital transducer (IDT). The IDT includes here gold thin-film printed electrical paths provided on a ZnO thin-film piezoelectric substrate 13.

The guidewire system 10 according to the embodiment allows integrating a sensor device 12 in a guidewire 11 without changing the haptic feel of the guidewire 11. The unamended haptic feel and the improved handiness can be used to locate and/or classify a stenosis or another disease state within arteries and/or veins. The haptic feel may also be used to determine a location for an implantable device within the vasculature, such as a stent, a heart valve or the like.

Figure 3:
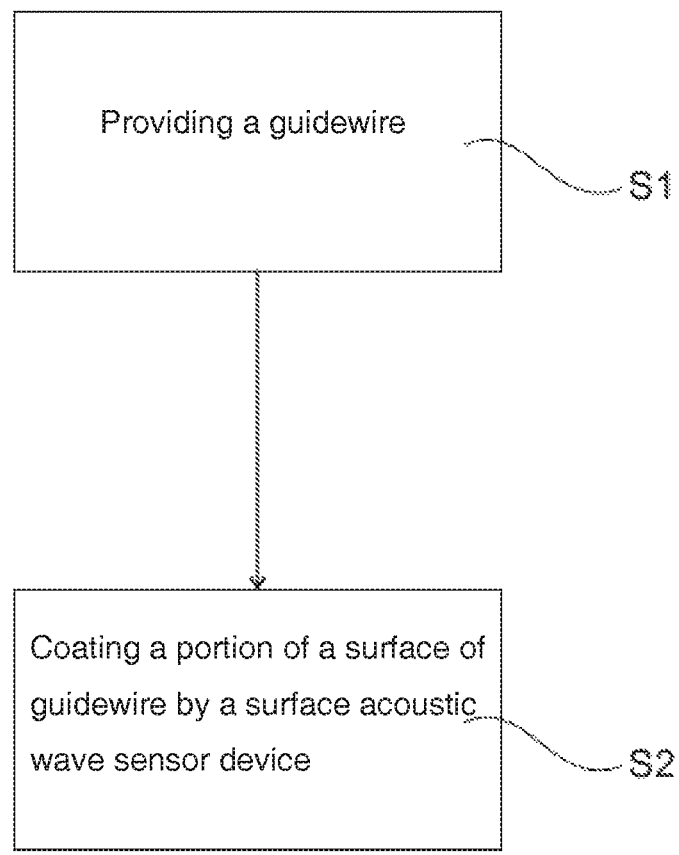
FIG. 3 illustrates basic steps of an example of a method for manufacturing a guidewire system according to one embodiment.

FIG. 3 illustrates a schematic overview of steps of a method for manufacturing a guidewire system 10. The method includes the following steps, not necessarily in this order:

In a first step S1, providing a guidewire 11, and

In a second step S2, coating a portion of a surface of the guidewire 11 by a surface acoustic wave sensor device 12.

The sensor device 12 includes a piezoelectric substrate 13 and a transducer 14. The thickness of the sensor device 12 perpendicular to a longitudinal direction of the guidewire 11 is smaller than 100 µm.

The coating step maintains the cross section of the guidewire 11 by coating the guidewire 11 with the very thin sensor device 12 instead of for example, introducing a recess into the guidewire 11 for example, a larger sensor. The coating step also maintains the mechanical properties of the guidewire 11 by coating the guidewire 11 without the application of heat or other influences harming the guidewire materials or inducing micro structural transformations or defects. The coating step may be a sol-gel process or a sputtering process.

As the cross section and the mechanical properties of the guidewire 11 remain unamended, also the properties and, for example, the haptic feel of the entire guidewire system 10 is maintained, which eases the application by a user.

It has to be noted that embodiments are described with reference to different subject matters. For example, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While embodiments have been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed embodiment, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

What is claimed is:

1. A guidewire system, comprising:
    a guidewire; and
    a surface acoustic wave sensor device;
    wherein a portion of a surface of the guidewire is coated by the sensor device;
    wherein the sensor device comprises a piezoelectric substrate and a transducer; and
    wherein a thickness of the sensor device perpendicular to a longitudinal direction of the guidewire is smaller than 100 μm; and
    wherein the piezoelectric substrate of the sensor device is directly coated on the guidewire.

2. The guidewire system of claim 1, wherein the thickness of the sensor device perpendicular to a longitudinal direction of the guidewire is smaller than 50 μm.

3. The guidewire system of claim 1, wherein the guidewire system has a diameter in a range of 0.05 to 1 mm.

4. The guidewire system of claim 1, wherein the guidewire system has a diameter in a range of 0.1 to 0.5 mm.

5. The guidewire system of claim 1, wherein the piezoelectric substrate comprises zinc oxide, aluminium nitride, silicon dioxide, barium titanate, lead zirconate titanate, sodium potassium niobat and/or lithium niobat.

6. The guidewire system of claim 1, wherein the transducer comprises an interdigital transducer.

7. The guidewire system of claim 1, wherein the sensor device is directly coated on the guidewire.

8. The guidewire system of claim 1, wherein the sensor device is configured for measuring a pressure change in front and after a vasoconstriction.

9. A measuring system comprising:
    a guidewire system of claim 1; and
    a processing device;
    wherein the processing device is arranged distant to a sensor device of the guidewire system; and
    wherein the processing device is configured for a communication with the sensor device.

10. The measuring system of claim 9, wherein the processing device is configured for detecting a position of the sensor device.

* * * * *